United States Patent [19]

Christenson

[11] 4,053,459

[45] Oct. 11, 1977

[54] ANTIBODY SPECIFIC TO METHAQUALONE AND ITS METABOLITES

[75] Inventor: James Gordon Christenson, North Caldwell, N.J.

[73] Assignee: Hoffmann-La Roche Inc., Nutley, N.J.

[21] Appl. No.: 616,451

[22] Filed: Sept. 24, 1975

[51] Int. Cl.² ............... A61K 37/06; C07D 239/00
[52] U.S. Cl. .................. 260/112 B; 260/112 R; 260/121; 260/251 QA; 260/256.4 Q; 424/1; 424/8; 424/12; 424/85; 424/88; 424/251
[58] Field of Search ............... 424/8, 12, 1, 251, 85, 424/88; 260/251 QA, 256.4 Q, 112 B, 121, 112 R

[56] References Cited

U.S. PATENT DOCUMENTS 3,690,834  9/1972  Goldstein .................. 424/12 X

*Primary Examiner* — Albert T. Meyers
*Assistant Examiner* — A. P. Fagelson
*Attorney, Agent, or Firm* — Samuel L. Welt; George M. Gould

[57] ABSTRACT

A sensitive radioimmunoassay for methaqualone and its major metabolites is described. Included within this disclosure is the preparation of novel methaqualone haptens, the preparation of antigens from such haptens by coupling to an immunogenic carrier material, the use of such antigens to elicit antibodies selective to methaqualone and its major metabolites and an improved radiolabelled derivative of a methaqualone analog used in the practice of said radioimmunoassay.

3 Claims, No Drawings

ANTIBODY SPECIFIC TO METHAQUALONE AND ITS METABOLITES

BACKGROUND OF THE INVENTION

Methaqualone is a sedative-hypnotic drug having the chemical name 2-methyl-3-o-tolyl-4(3H)-quinazolinone. It was introduced on the United States market in 1965 and, according to some recent commentators, has become subject to considerable abuse (Smith and Wesson, *Ann. Rev. Pharmacol,* 14, 513 (1974).

Methaqualone is apparently extensively metabolized so that very little unchanged methaqualone is found in the urine. The metabolites are mostly glucuronides of monohydroxylated derivatives (Bonnichsen et al., *Clin. Chim. Acta.,* 40, 309 (1972). Hydroxylation occurs mainly at the 3- and 4 -positions and on the methyl group of the tolyl moiety. It appears that the quinazoline ring system is largely unmodified in the metabolites.

SUMMARY OF THE INVENTION

An antigen capable of eliciting antibodies specific for methaqualone and its metabolites when injected into a mammalian host is readily prepared by utilizing the known 2-methyl-3-(2-methyl-4-aminophenyl)-3,4-dihydro-4-quinazolinone to form a N-carbonyl-lower alkylenecarboxyl analog of methaqualone and then covalently coupling such hapten to an immunogenic carrier material through the carboxyl moiety of the hapten and reactive amino or hydroxyl groups on the carrier material. In addition, a radiolabeled methaqualone derivative useful in conducting the methaqualone radioimmunoassay is prepared using the 4-hydroxyphenyl derivative (a known metabolite of methaqualone) as the substrate.

DESCRIPTION OF THE INVENTION

The present invention relates in one aspect to a novel antigen comprising methaqualone coupled to an immunogenic carrier material through a carbonyl lower alkylene carbonyl linking group. This antigen is conveniently prepared by reacting the primary amino group of a 4-aminophenyl methaqualone analog with a lower alkylene dicarboxylic acid or activated functional derivative thereof, e.g., anhydride, mono-p-nitrophenyl ester, carbonyl halide or the like. The resulting N-carbonyl-lower alkylenecarboxyl derivative (hapten) is then covalently bonded through the free carboxyl group to available amino or hydroxy groups in the immunogenic carrier material to form the desired antigen. In such manner the important antigenic determinant sites on the quinazoline ring system of methaqualone are not affected.

As used herein the term "immunogenic carrier material" is meant to include those materials which have the property of independently eliciting an immunogenic response in a host animal when injected therein and which can be coupled by covalent bonding to said methaqualone hapten. Suitable carrier materials include, for example, materials such as proteins; natural or synthetic polymeric compounds such as polypeptides, e.g., polylysine; polysaccharides; and the like. A particularly preferred carrier material for the practice of the present invention is a protein.

The identity of the protein carrier material utilized in the preparation of the instant antigen is not narrowly critical. Examples of preferred proteins useful in the practice of this invention include the serum proteins preferably mammalian serum proteins, such as, for example, human gamma globulin, human serum albumin, rabbit serum albumin, bovine gamma globulin and bovine serum albumin. Other suitable protein products will be suggested to one skilled in the art. It is generally preferred that proteins be utilized which are foreign to the animal host in which the resulting antigen will be employed.

The first step in the preparation of the subject antigen involves reacting 2-methyl-3-(2-methyl-4-aminophenyl)-3,4-dihydro-4-quinazolinone with a lower alkylene dicarboxylic acid or activated derivative thereof as described above. Preferably the lower alkylene moiety will be straight chained and have from 1 to 6 carbon atoms. Additionally, in the preferred aspect of the invention the anhydride derivative is utilized. Succinic anhydride is the compound of choice for this purpose.

The reaction between the lower alkylene dicarboxylic acid or derivative thereof and the 4-aminophenyl compound can be carried out in conventional manner. Thus, for example, succinic anhydride will react with the 4-aminophenyl compound in an inert organic solvent such as an aromatic hydrocarbon such as benzene, xylene or toluene at reflux to produce the N-succinamic acid derivative.

The use of a succinamic acid derivative is merely convenient in the present invention. Other means of introducing "spacing" groups between the important haptenic determinants and the immunogenic carrier are well known. For example, alkylation of methaqualone by Friedel-Crafts reactions with haloalkanoic acid esters or alkylation of alkali metal salts of phenolic methaqualone derivatives by haloalkanoic acid esters would yield, after hydrolysis of the esters, compounds comparable to the hapten described herein. Another alternative aspect involves the direct synthesis of a methaqualone hapten from N-acetylanthranilic acid and an ester of 4-lower alkyl carboxy-2-methylaniline followed by ester hydrolysis.

It is preferred that the spacing groups used in the present invention contain from 2 to 7 carbon atoms in the linking chain. Preferably the spacing groups will be substituted in the methaqualone molecule in the tolyl group para to the tertiary nitrogen atom.

Examples of alternative compounds useful as haptens herein are 2-methyl-3-[2-methyl-4-(2-carboxyethoxy)-phenyl]-3,4-dihydro-4-quinazolinone and 2-methyl-3-[2-methyl-4-(2-carboxyethyl)phenyl]-3,4-dihydro-4-quinazolinone.

Thus in generic terms the haptens of the present invention will be seen to comprise a methaqualone radical having a spacing group bonded thereto through the tolyl ring, said spacing group consisting of an amino carbonylalkylenecarboxy, an oxylower alkylene carboxy or a lower alkylene carboxy group.

The resulting hapten can then be coupled to the immunogenic carrier material by any of several procedures known in the art for this purpose.

One such procedure involves the use of a coupling agent such as a water soluble carbodiimide, such as for example, 1-ethyl-3-(3-dimethylaminopropyl)-carbodiimide. The resulting anitgen can be purified from unreacted starting materials and low molecular weight byproducts by conventional separation techniques such as dialysis.

An alternate technique known in the art involves the use of a mixed anhydride. Such procedure employs a tri-lower alkylamine, i.e., triethylamine and a lower alkyl fluoroformate to form the desired reagent solution with the hapten in a cyclic ether solvent, such as in dioxane. This solution is then added to an aqueous solution of the immunogenic carrier material which may also contain the cyclic ether solvent for improved solubility of the activated hapten. This reaction is preferably conducted at temperatures below room temperature, i.e., about 8° 1 C. A basic pH such as about 9 is desirable for this reaction. As above, the antigen may be isolated by conventional procedures.

The attachment of the methaqualone hapten by the carbodiimide method to bovine serum albumin as a representative immunogenic carrier material has been found to be about 18–25 mole equivalents per mole of protein.

The antigen of the present invention may then be utilized to induce formation of antibodies specific for methaqualone and methaqualone metabolites in the serum of host animals by injecting the antigen in such host. The collected serum may be used per se as a methaqualone specific antiserum or, if desired, the antibodies therein may be further purified, for example, by precipitation with a neutral salt solution followed by dialysis and column chromatography, or by other means known in the art.

Suitable host animals for preparing antiserum to methaqualone include mammals such as rabbits, horses, goats, guinea pigs, rats, cows, sheep and the like. The resulting antibodies will have a multiplicity of active sites which will selectively complex with methaqualone, the methaqualone antigen of the present invention or closely related derivatives of methaqualone such as the major metabolites of methaqualone.

The specific antibodies of the present invention are useful as reagents in biochemical assays for the determination of the presence of methaqualone and its metabolites in biological fluids. A particularly preferred assay procedure is the immunoassay procedure such as described in U.S. Pat. No. 3,709,868. Preferred labeled methaqualone derivatives for use in immunoassays include isotopically labeled methaqualone derivatives, particularly, $^{125}$I-2-methyl-3-(2-methyl-4-hydroxyphenyl)-4-(3H)-quinazolinone, as well as methaqualone labeled with an electron spin resonance group. Examples of the use of the various electron spin resonance labeled molecules in bioassays are to be found in U.S. Pat. Nos. 3,453,288, 3,481,952 and 3,507,876.

The radioimmunoassay method is preferred for the determination of methaqualone and its metabolites. It is a sensitive, simple, rapid and reproducible procedure.

EXAMPLE 1

Preparation of antigen

To 100 mg. of bovine serum albumin ("crystalized"; $1.47 \times 10^{-6}$ mole) in 10 ml. of water was added 29.8 mg. ($8 \times 10^{-5}$ mole) of N-[3-methyl-4-(2-methyl-4-oxo-3,4-dihydroquinazolin-3-yl)phenyl] succcinamic acid in 0.5 ml of N-methylpyrrolidone. The combined solution was adjusted to pH 5.5 with 0.1 N HCl or 0.1 N NaOH. To this solution was added 15.4 mg. ($8 \times 10^{-5}$ mole) of 1-ethyl-3-(3-dimethylaminopropyl)carbodiimide hydrochloride all at once, with magnetic stirring. This solution was stirred for four hours while the pH was maintained between 5.5 and 6.0 with 0.1 N HCl. The reaction mixture was allowed to stand overnight at 4°, then dialyzed overnight against one 1 of deionized water. The dialysate was then changed and dialysis continued for several hours. The desired antigen is recovered from the dialysis bag.

The degree of incorporation of the hapten in two immunogen preparations was found to be 18–25 mole equivalents of methaqualone per mole of BSA.

EXAMPLE 2

Immunization and Bleeding

For immunization of goats, the dialyzed antigen material of Example 1 was diluted with phosphate buffered saline to a protein concentration of approximately 2mg/ml. The diluted immunogen was then emulsified with an equal volume of Freund's adjuvant. The first three inoculations (using complete adjuvant) were administered at weekly intervals, the fourth after another three weeks, and monthly thereafter (the fourth and successive inoculations used incomplete adjuvant). Each inoculation comprised two subcutaneous injections of 0.5 ml. each.

Test bleedings were taken at two, three, and four weeks after the first inoculation. After five weeks, and at biweekly intervals thereafter, 300 ml. of blood was drawn and serum prepared by standard techniques.

EXAMPLE 3

N-[3-Methyl-4-(2-methyl-4-oxo-3,4-dihydro-quinazolin-3-yl)-phenyl]succinamic acid Into a 1-l. flask equipped with a Dean-Stark trap, and under nitrogen was placed 12.0 g. (0.045 mole) of 2-methyl-3-(2-methyl-3-aminophenyl)-3,4-dihydro-4-quinazolinone and 300 ml. of benzene. Upon refluxing for 3 hours, traces of water were collected in the trap. After cooling to room temperature, 4.8 g. (0.048mole) of succinic anhydride was added and the mixture refluxed with stirring overnight. Upon cooling and filtration, the solid obtained was washed with benzene and dried in vacuo at 50°, to give 13.1g., of a solid m.p. 202.5–203.5° (dec.). The solid was then slurried in 150 ml. of water at 60° for 30 minutes filtered, washed with a little water and dried in vacuo at 50°. It was then refluxed in 1. 1 of acetonitrile for 40 minutes, allowed to cool to room temperature and filtered, to give, when dried in vacuo at 50°, 9.1 g of the above-titled compound, m.p. 228.5–229.50, 55% of theory.

Anal. Calcd. for $C_{20}H_{19}N_3O_4$: C, 65.75; H, 5.24; N, 11.50. Found: C, 65.67; H, 5.11; N, 11.70.

EXAMPLE 4

Preparation of $^{125}$I-labeled Methaqualone Derivative

2-Methyl-3-(2-methyl-4-hydroxyphenyl)-4(3H)-quinazolinone was dissolved in dimethylsulfoxide to a concentration of 2 mg/ml, then diluted with an equal volume of water. This solution was then used for iodination using Na$^{125}$I and chloramine-T under conventional conditions.

ASSAY PROCEDURE

The assay procedure is similar to that used in the ABUSCREEN Radioimmunoassay for morphine. The sample volume required for the assay is 0.1 ml. For quantitative evaluation, standard curves are prepared on rectangular coordinates using 1000, 500, 250, 100, 50, 25, and 10 ng of methaqualone per ml of normal human urine.

PERFORMANCE OF THE ASSAY

The assay method in general involves mixing a sample containing methaqualone and/or its metabolites with a known amount of the labeled methaqualone derivative and the methaqualone selective antibody, measuring the degree of binding of the labeled methaqualone derivative and determining the amount of methaqualone and/or its metabolites present in said sample by c comparing said degree of binding to a standard curve obtained by mixing known amounts of methaqualone and/or its metabolites with fixed amounts of said labeled methaqualone derivative and said antibody and determining the degree of binding for each known amount of methaqualone and/or its metabolites. Methaqualone was chosen for standardization, in spite of the fact that very little of this drug is excreted per se in the urine, because of quantitative and qualitative variations in the pattern of excretion of metabolites among individuals. Because of these variations, it is unlikely that the validity of the assay could be improved by selection of a metabolite or combination of metabolites for standardization. Results are thus as expressed "methaqualone equivalents" in ng. per ml. of urine.

Methaqualone standards were prepared by diluting a 1 mg/ml. solution of methaqualone in 50% dimethylsulfoxide to the required concentration with normal human urine (the minimal dilution required is 2000-fold, so the amount of dimethylsulfoxide present in the standards is considered negligible).

From the standard curve obtained, it is clear that the assay can readily detect methaqualone levels on the order of 10 ng of methaqualone in 0.1 ml. of urine (100 ng/ml).

A study designed to test the performance of the methaqualone assay under field conditions was undertaken. Healthy male and female volunteers were administered single oral doses of either methaqualone or one of fifteen other drugs thought to be potential cross-reactants because of their chemical or pharmacologic properties. The total excreted urine was then collected at various time intervals for five days and specimens were assayed for the presence of methaqualone, its metabolites, or cross-reacting substances. The results, shown in Table I, indicate that none of the urines obtained before ingestion of drug or after ingestion of any drug other than methaqualone assayed at greater then 39 ng/ml. of methaqualone equivalents. The urines from those subjects who received methaqualone, however, tested at greater than 500 ng/ml within one hour of ingestion and remained above this level for the duration of the experiment.

TABLE I

| Subject | Drug (generic) | Dose (mg) | Methaqualone Equivalents (ng/ml) in urine collected during specified time interval (hr) | | | | | | | | | |
|---|---|---|---|---|---|---|---|---|---|---|---|---|
| | | | 0 | 0–1 | 1–4 | 4–8 | 8–12 | 12–24 | 24–48 | 48–72 | 72–96 | 96–120 |
| A | Methaqualone | 150 | 7 | >500 | >500 | >500 | >500 | >500 | >500 | >500 | >500 | >500 |
| B | Methaqualone | 150 | 39 | >500 | >500 | >500 | >500 | >500 | >500 | >500 | >500 | >500 |
| C | Methaqualone | 300 | 8 | >500 | >500 | >500 | >500 | >500 | >500 | >500 | >500 | >500 |
| D | Methaqualone | 300 | 5 | >500 | >500 | >500 | >500 | >500 | >500 | >500 | >500 | >500 |
| E | Methyprylon | 300 | 20 | 0 | 20 | 0 | 12 | 10 | 0 | 0 | 7 | |
| F | Methyprylon | 300 | 0 | 0 | 0 | 0 | 0 | 0 | 0 | 0 | 0 | 0 |
| G | Aprobarbital | 40 | 11 | 7 | 0 | 0 | 0 | 0 | 0 | 2 | 9 | 0 |
| H | Aprobarbital | 40 | 9 | 11 | 0 | 0 | 0 | 0 | 0 | 0 | 0 | 0 |
| I | Phenobarbital Sodium | 64 | 17 | 0 | 0 | 0 | 0 | 0 | 0 | 1 | 0 | 6 |
| J | Phenobarbital Sodium | 64 | 0 | 0 | 0 | 0 | 0 | 0 | 0 | 10 | 3 | 11 |
| K | Secobarbital Sodium | 100 | 0 | 0 | 0 | 0 | 0 | 22 | 20 | 16 | 16 | 2 |
| L | Secobarbital Sodium | 100 | 0 | 0 | 0 | 0 | 0 | 0 | 0 | 17 | 0 | 0 |
| M | Glutethimide | 500 | 15 | 0 | 14 | 24 | 24 | 14 | 30 | 32 | 15 | 3 |
| N | Glutethimide | 500 | 0 | 0 | 0 | 0 | 7 | 11 | 7 | 18 | 26 | 13 |
| O | Diphenylhydantoin Sodium | 100 | 0 | 0 | 0 | 0 | 0 | 0 | 0 | 0 | 0 | 0 |
| P | Diphenylhydantoin Sodium | 100 | 0 | 0 | 0 | 5 | 0 | 0 | 0 | 0 | 2 | 17 |
| Q | Primadone | 250 | 0 | 0 | 0 | 0 | 0 | 0 | 12 | 0 | 0 | 0 |
| R | Primadone | 250 | 0 | 0 | 1 | 0 | 15 | 0 | 0 | 0 | 6 | 3 |
| S | Diazepm | 10 | 0 | 0 | 0 | 0 | 0 | 0 | 0 | 0 | 0 | 0 |
| T | Diazepam | 10 | 4 | 0 | 0 | 0 | 0 | 0 | 0 | 2 | 2 | 0 |
| U | Oxtriphylline | 200 | 3 | 0 | 0 | 0 | 0 | 0 | 0 | 0 | 4 | 0 |
| V | Oxtriphylline | 200 | 1 | 0 | 0 | 0 | 0 | 5 | 0 | 4 | 1 | 0 |
| W | Caffeine, citrated | 25 | 0 | 0 | 0 | 0 | 0 | 0 | 0 | 0 | 0 | 10 |
| X | Caffeine, citrated | 250 | 4 | 0 | 0 | 1 | 1 | 3 | 10 | 10 | 6 | 5 |
| Y | Thioridazine Hydrochloride | 25 | 15 | 23 | 4 | 5 | 10 | 11 | 11 | 14 | 13 | 11 |
| Z | Thioridazine Hydrochloride | 25 | 4 | 0 | 0 | 8 | 8 | 2 | 6 | 10 | 14 | 14 |
| AA | Quinine Sulfate | 325 | 1 | 0 | 0 | 0 | 2 | 4 | 0 | 0 | 1 | 0 |
| BB | Quinine Sulfate | 325 | 3 | 0 | 0 | 3 | 0 | 2 | 1 | 2 | 0 | 0 |
| CC | Imipramine-HCl | 25 | 3 | 4 | 2 | 4 | 4 | 3 | 1 | — | — | — |
| DD | Imipramine-HCl | 25 | 0 | 0 | 0 | 0 | 0 | 0 | 0 | 2 | 3 | 0 |
| EE | Phenylbutazone | 100 | 0 | 0 | 0 | 0 | 0 | 1 | 1 | 1 | 0 | 0 |
| FF | Phenylbutazone | 100 | 0 | 0 | 0 | 1 | 3 | 0 | 3 | 1 | 4 | 3 |
| GG | Flurazepam-HCl | 30 | 0 | 0 | 0 | 0 | 0 | 0 | 0 | 1 | 1 | 1 |
| HH | Flurazepam-HCl | 30 | 0 | 0 | 0 | 0 | 0 | 0 | 0 | 0 | 0 | 0 |

I claim:

1. An antibody specific to methaqualone and its metabolites prepared by innoculating a host animal with an antigen consisting essentially of a methaqualone hapten having a methaqualone radical bonded to a spacing group through the tolyl ring of said methaqualone radical, said spacing group being selected from the group consisting of an amino carbonylalkylene carboxy, an oxyloweralkylene carboxy and a lower alkylenecarboxy group and having from 2 to 7 carbon atoms in the linking chain, said hapten being covalently bonded to an immunogenic carrier material through the carboxyl group of said spacing group.

2. The antibody of claim 1 wherein the hapten of said antigen is a N-carbonyl-lower alkylenecarboxyl derivative of 2-methyl-3-(2-methyl-4-aminophenyl)-3,4-dihydro-4-quinazolinone.

3. The antibody of claim 2 wherein said carbonyl-lower alkylenecarboxyl group is succinyl.

* * * * *